United States Patent
Zhang et al.

(10) Patent No.: US 10,368,966 B2
(45) Date of Patent: Aug. 6, 2019

(54) 7-WAY DENTAL SYRINGE

(71) Applicants: Winston Zhang, Irvine, CA (US); Paymon Parish Sedghizadeh, Playa Vista, CA (US); Grace Yu Zhang, Irvine, CA (US)

(72) Inventors: Winston Zhang, Irvine, CA (US); Paymon Parish Sedghizadeh, Playa Vista, CA (US); Grace Yu Zhang, Irvine, CA (US)

(*) Notice: Subject to any disclaimer, the term of this patent is extended or adjusted under 35 U.S.C. 154(b) by 0 days.

(21) Appl. No.: 16/257,612

(22) Filed: Jan. 25, 2019

(65) Prior Publication Data

US 2019/0151057 A1     May 23, 2019

(51) Int. Cl.
*A61C 17/02* (2006.01)
*A61C 17/022* (2006.01)

(52) U.S. Cl.
CPC ........ *A61C 17/0202* (2013.01); *A61C 17/022* (2013.01); *A61C 17/0217* (2013.01); *A61C 17/0211* (2013.01)

(58) Field of Classification Search
CPC .................. A61C 17/0202; A61C 17/0217
See application file for complete search history.

(56) References Cited

U.S. PATENT DOCUMENTS

| | | | | |
|---|---|---|---|---|
| 3,874,083 A | * | 4/1975 | Buckley | A61C 17/0217 433/80 |
| 4,149,315 A | * | 4/1979 | Page, Jr. | A61C 17/0217 222/571 |
| 4,227,878 A | * | 10/1980 | Lohn | A61C 17/0217 433/80 |
| 5,848,893 A | * | 12/1998 | Martin | A61C 17/02 433/80 |
| 5,868,571 A | * | 2/1999 | Nakanishi | A61C 1/18 433/115 |
| 6,093,020 A | * | 7/2000 | Pond | A61C 17/0202 433/80 |
| 9,173,725 B2 | * | 11/2015 | Thorp | A61C 17/0202 |
| 9,795,464 B2 | * | 10/2017 | Wang | A61C 17/0202 |
| 2017/0224452 A1 | * | 8/2017 | Chang | A61C 17/02 |

* cited by examiner

*Primary Examiner* — Ralph A Lewis

(57) ABSTRACT

A 7-way dental syringe is a device in a dental delivery system that delivers an air stream, water stream, air spray and water spray; four efficient ways to clean a patient's mouth. Additionally, the 7-way dental syringe is a controllable pressurized dental water jet system. It can dislodge plaque biofilms from teeth and interdental regions, access a periodontal pocket to wash out plaque therein, and cleanse a tooth extraction site or irrigate exposed jawbone; various clinical ways to perform advanced oral hygiene.

1 Claim, 5 Drawing Sheets

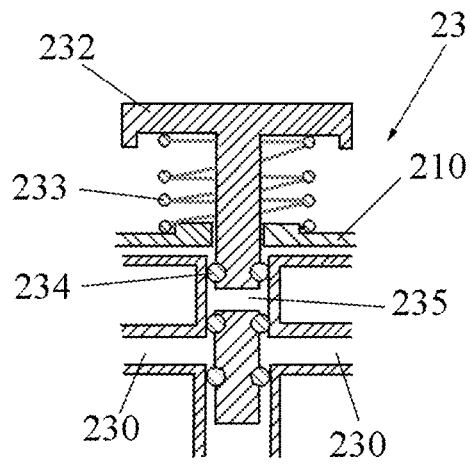
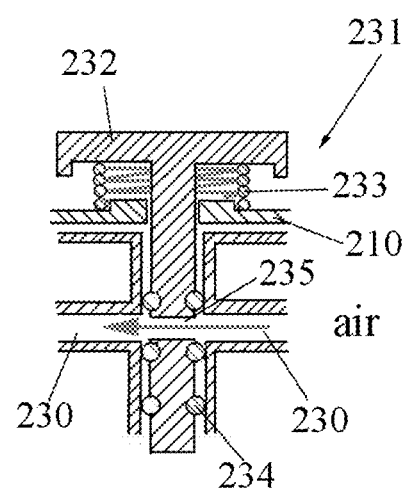
FIG. 3B
FIG. 3B-1
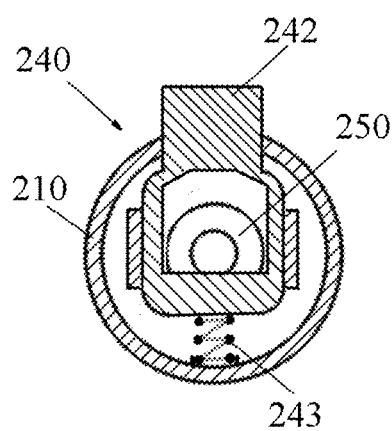
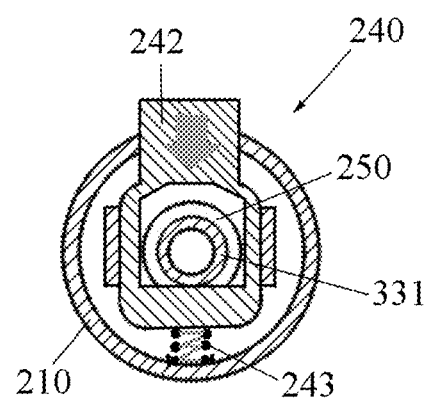
FIG. 3C
FIG. 3C-1

7-WAY DENTAL SYRINGE

FIELD OF INVENTION

The field of the invention is a dental syringe which is a device in a dental delivery system.

BACKGROUND OF THE INVENTION

Currently, a 3-way dental syringe is a standard device in a dental delivery system and widely used by dentists, orthodontists, oral surgeons, dental assistants, and dental hygienists. The 3-way dental syringe deliveries water, air, or mist to the patient's mouth to clean away debris from the area that the dentist is working on. The mist is inefficient for cleaning debris obviously.

Conventional tip in the 3-way dental syringe has an air channel with uneven diameters. An air blows the water to generate mist. Therefore, it produces inadequate air-flow and blows the water generates uneven mist. Many previous patent applications were trying to improve it.

The water jet technology has been widely used for cleansing in industries and a dental water jet system to blast away dental plaque has been verified by USC. A dental water jet system has been patented which opens periodontal pocket to wash and suck out the plaque therein, refer to the U.S. Pat. No. 10,064,710. Unfortunately the above two hydraulic technologies for oral hygiene did not widely used by dental professionals yet.

The present invention satisfies the shortcomings, limitations or disadvantages of the 3-way dental syringes in the market and patent proposals in the prior art.

CROSS REFERENCE

| U.S. Patent Documents | | |
|---|---|---|
| 5,236,356 | August 1993 | Davis et al. |
| 6,533,578 | March 2003 | Segal |
| 6,796,796 | September 2004 | Segal |
| 8,662,470 | March 2014 | Klecker et al. |
| 9,072,573 | July 2015 | Klecker et al. |
| 9,173,725 | November 2015 | Thorp et al. |
| 9,687,328 | June 2017 | Esrock |
| 9,795,464 | October 2017 | Wang et al. |
| 9,814,551 | November 2017 | Fournie et al. |
| 2013/0260333 | October 2013 | Berkely |
| 2013/0316299 | November 2013 | Berkely |

SUMMARY OF THE INVENTION

The present invention, a 7-way dental syringe, is a device in a dental delivery system. The 7-way dental syringe not only has four more efficient ways to delivery air, water to clean patient's mouth but also is a controllable pressurized dental water jet system. It can dislodge plaque biofilms from teeth and interdental regions, access a periodontal pocket to wash out plaque therein, and cleanse a tooth extraction site or a exposed jawbone; various clinical ways to perform advanced oral hygiene.

The 7-way dental syringe comprises a 2 holes tubing, a handle, and a tip. The fluid from a dental delivery system through the 2 holes tubing flows into a fluid passageway inside the handle then eject out from the tip to the patient's mouth.

The 2 holes tubing is a twin hoses in different sizes instead of same sizes in the 3-way dental syringe. An air hose's internal diameter is about 1-2 mm and a water hose's internal diameter is about double length of the internal diameter of the air hose. The regular pressure of the air and water from the dental delivery system will be 45-50 PSI.

The handle is for a dentist to hold onto and comprises a fluid passageway inside the handle and a tip connector. The fluid passageway merged from an air passageway and a water passageway. The air passageway connects the air hose in the 2 holes tubing, the air flows into the air passageway then out from the fluid passageway to the tip. The air passageway has an On-Off valve. The water passageway connects the water hose in the 2 holes tubing, the water flows into the water passageway then out from the fluid passageway to the tip. The water passageway has a volume controllable valve for adjust pressure of the tip's outlet. The tip connector is a latch lock connector instead of a ball connector which is popularly used in the 3 ways dental syringe. The latch lock connector could avoid the tip freely rotating.

The tip comprises a bent pipe, a twist generator and an inserting section. The inserting section inserts the tip into the handle and fluidly connects the fluid passageway in the handle. The twist generator comprises a distal close-off end of the pipe with a male external thread, a cap with internal thread and a pinhole centrally located at a top of the cap, has a mechanism to divide single fluid flow into two separate flows that twist with respect to each other. An air or water ejects out from the pinhole to form various shapes such as a twisted beam, a twisted cone and twisted stream depend on how tight the cap screwed against the pipe.

For oral hygiene purpose user should fully open the water valve and the water eject out from the pinhole could have higher pressure such as 90 PSI; (1) when the cap is screwed loose against the pipe, water ejects out from the pinhole in the form of a twisted jet beam that blast away the plaque from teeth and interdental regions; (2) when the cap is screwed midway against the pipe, water ejects out from the pinhole in the form of a twisted stream that cleanse a tooth extraction site or irrigate an exposed jawbone; (3) when the cap is screwed tightly against the pipe, water ejects out from the pinhole in the form of a wide cone shaped rotating water wheels that can wash out any plaque therein and suck out any plaque therein.

For air/water cleans a patient's mouth: (1) an air stream: set the cap is screwed loose against the pipe then pushes the air button; (2) an air spray: set the cap is screwed tighten against the pipe, then pushes the air button; (3) a water stream: set the cap is screwed loose against the pipe, then slides the water valve's button to the midway; (4) a water spray: set the cap is screwed tighten against the pipe, then slides the water valve's button to the midway.

Various objects, features, aspects and advantages of the present invention will become more apparent from the following detailed description of preferred embodiments of the invention, along with the accompanying drawings in which like numerals represent like components.

BRIEF DESCRIPTION OF THE DRAWINGS

FIG. 3-1 is a schematic showing of the fluid passageway in the handle.

FIG. 3A-1 is a cross-section view of the water valve inside the handle at full open position.

FIG. 3B is a cross-section view of the air valve inside the handle.

FIG. 3B-1 is a cross-section view of the air valve inside the handle at opening position.

FIG. 3C is a cross-section view of the tip connector in the handle.

FIG. 3C-1 is a cross-section view of a tip is latched in the tip connector in the handle.

DESCRIPTION OF THE PREFERRED EMBODIMENTS

Figure 1:
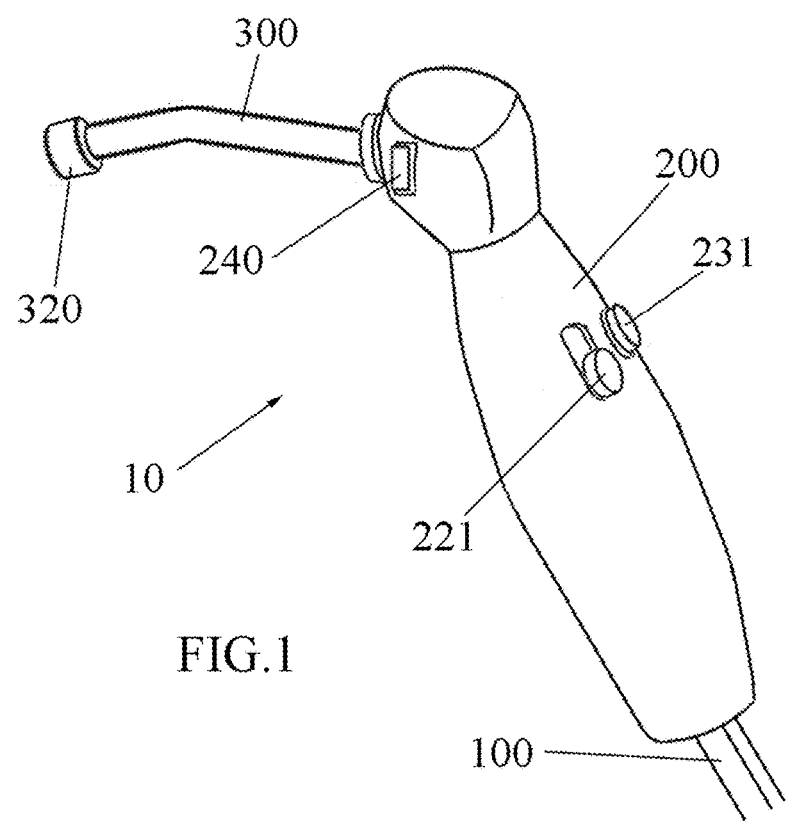
FIG. 1 is a schematic showing the 7-way dental syringe.

An embodiment of a 7-way dental syringe 10 is showing in FIG. 1. The 7-way dental syringe 10 comprises a two holes tubing 100, a handle 200, and a tip 300.

Figure 2:
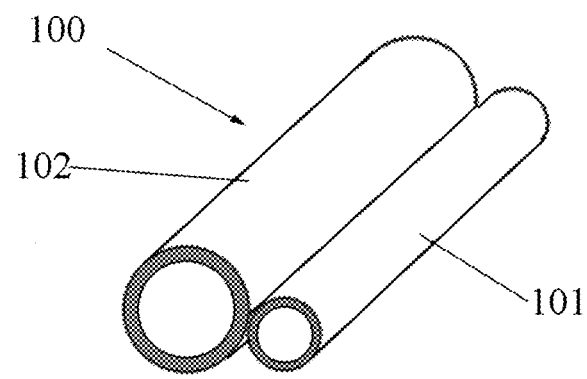
FIG. 2 is a schematic showing a 2 holes tubing.

The two holes tubing 100 is a conduit between the 7-way dental syringe 10 and a dental delivery system. The two holes tubing 100 is a twin hoses: an air hose 101 and a water hose 102. The internal diameter of the air hose 101 is about 1-2 mm. The internal diameter of a water hose 102 is about double length of the internal diameter of the air hose, refer to FIG. 2.

Figure 3:
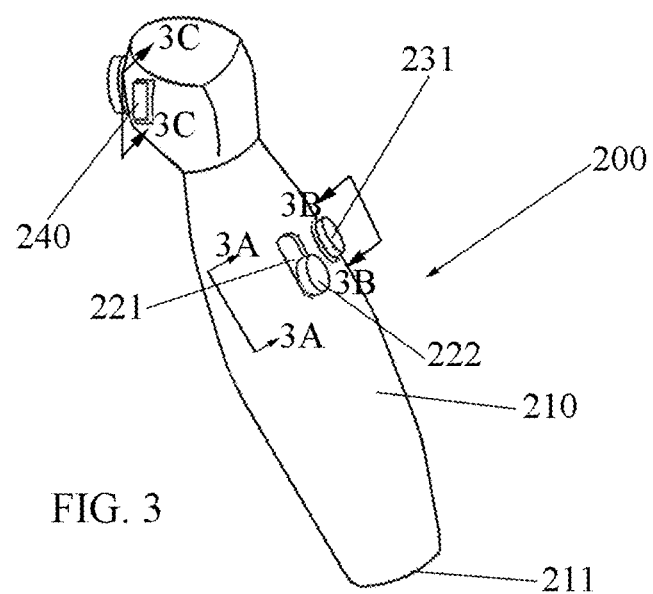
FIG. 3 is a schematic showing the handle.
Figures 1, 3:
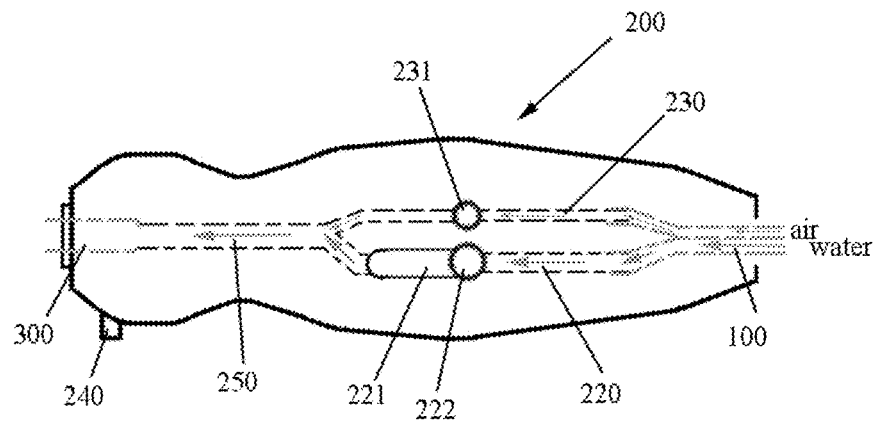

An embodiment of the handle 200 comprises a body 210, a tip connector 240, a tubing entry 211 and a fluid passageway 250 inside the handle 200 refer to FIG. 3 and FIG. 3-1. In the distal end of the handle 200 has the tip connector 240 for a tip 300 inserting into the handle 200. The tip connector 240 is controlled by a latch 242. In another end of the handle 200 has a tubing entry 211 for the two holes tubing 100.

The fluid passageway 250 inside the handle 200 comprises a water passageway 220 and an air passageway 230. The water passageway 220 has a water valve 221 and operating by a water button 222. The air passageway 230 has an air valve 231 and operating by an air button 232. The water passageway 220 and the air passageway 230 merged after the valves refer to the FIG. 3-1.

Figures 1, 3A:
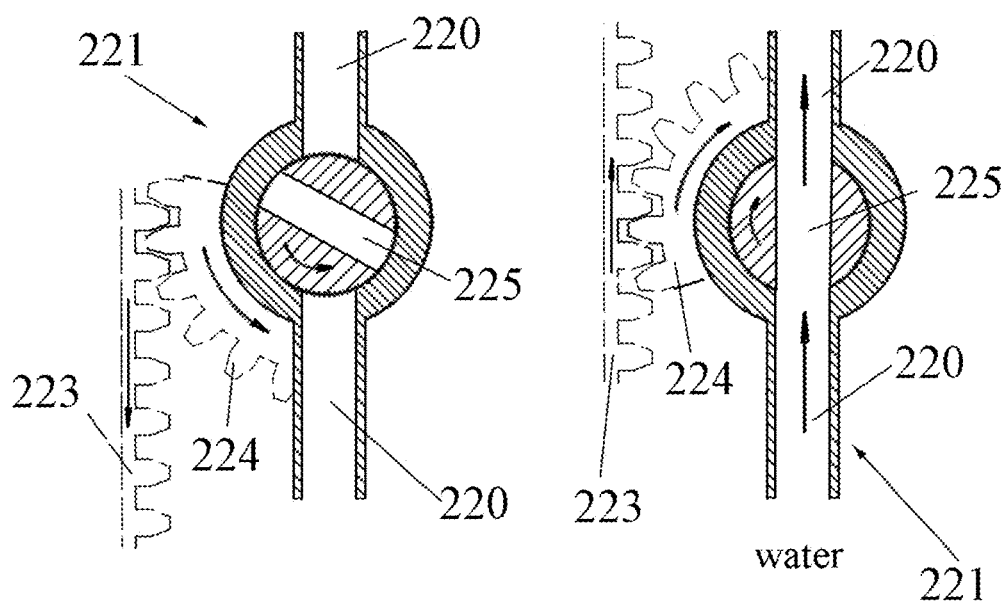
FIG. 3A is a cross-section view of the water valve inside the handle.

The water valve 221 is a volume controllable valve. A preferred embodiment of water valve comprises a slidable water button 222, a rack gear 223, a rotatable valve spool 225 with a gear portion 224 etc. and illustrating in FIG. 3, FIG. 3-1 FIG. 3A and FIG. 3A-1. The water button 222 is fixed to the rack gear 223. The water button 222 can be sliding forward and backward along the direction of the handle 200. When the water button 222 is moving, the rack gear 223 is also moving in the same direction and distance. The rack gear 223 drives the valve spool 225 rotating by the gear portion 224. When the water button 222 is backward to the original position the valve spool 225 is move away from the water passageway 220 and the water valve 221 is shut off, refer to FIG. 3A. When the water button 222 is sliding forward to the far end position, the valve spool 225 is fully connected with two sides of the water passageway 220 and the water valve 221 is fully open, refer to FIG. 3A-1. The user can set the water button 222 at anywhere in the sliding way for adjusting the water pressure of the tip 300.

The air valve 231 is an On-Off valve. A preferred embodiment of an air valve comprises an air button 232, a spring 233, a valve spool 235 and O-ring gaskets 234 etc. illustrating in FIG. 3, FIG. 3B and FIG. 3B-1. When the air button 232 is in the original position or the user released the air button 232, the valve spool 235 is away from the air passageway 230 by the force of spring 233 refer to FIG. 3B. When the user pushes the air button 232, the valve spool 235 connects the two sides of the air passageway, refer to FIG. 3B-1.

A preferred embodiment of the tip connector 240 is a latch lock connector and illustrated in the FIG. 3, FIG. 3C and FIG. 3C-1. The tip connector 240 strides across the fluid passageway 250 and comprises a sliding latch 242, a spring 243 etc. refer to FIG. 3C. When the user pushes the latch 242, the tip 300 can be inserted into the handle 200. Then the user released the latch 242, the latch 242 locked the groove 331 and the tip 300 is fluidly, leak-proof connecting to the fluid passageway 250 showing in the FIG. 3C-1. The tip 300 can be manually but not freely rotating like ball connector does. It is important for oral hygiene.

Figure 4:
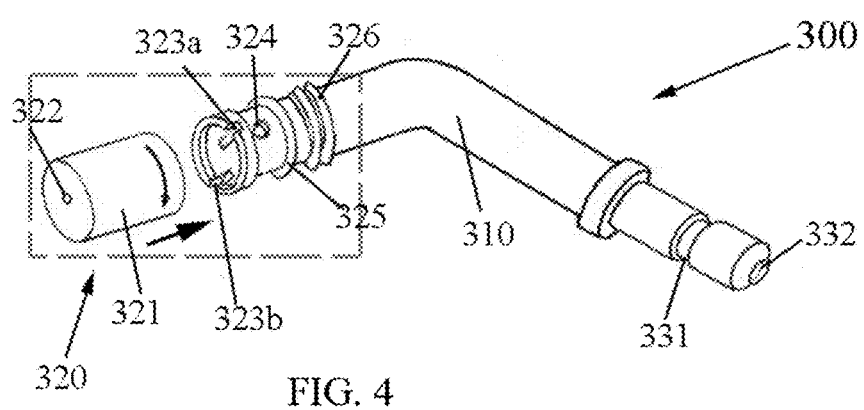
FIG. 4 is a schematic showing the tip.

An embodiment of the tip 300, refer to FIG. 4, comprises a bent pipe 310, a twist generator 320 at distal end of the pipe 310, a groove 331 and an inlet 332. The twist generator comprises a distal close off end of the pipe with a male external thread 326, a cap 321 with internal thread and a pinhole 322 at top center of the cap 321, a pair parallel lifting lines 323a and 323b are layout on the close off end of the pipe 310, a pair of fluid ejecting holes 324 in the wall of pipe 310, the pair is opposite each other and only one can be seen in the FIG. 4, An O-ring gasket 325, an external thread 326 that matches internal thread inside the cap 321.

A flow of fluid in the pipe 310 ejects out through the pair ejecting holes 324 become two flows. The fluid are blocked by the O-ring gasket 325 then flow through the two lifting lines 323a and 323b that twist with respect to each other and eject out from the pinhole 322.

For delivery air/water to clean patient's mouth, user can push air valve button 232 or sliding water valve button 222 to the midway in the handle 200. When the cap 321 is screwed slightly loose against the pipe 310, a fluid stream will eject out from pinhole 322; and the cap 321 is screwed tighten against the pipe 310, the fluid spray exiting out from the pinhole 322. There are 4 ways to do so.

Additional, when the water valve 222 is full opened, the 7-way dental syringe has 3 more ways to perform advanced oral hygiene. when the cap 321 is screwed loose against the pipe 310, a water will eject out from the pinhole 322 and forms a twisted jet beam that can blast away plaque in tooth and interdental area; When the cap 321 is screwed tighten against the pipe 310, the water twist exits out from the pinhole 322 and forms a wide cone shaped rotating water wheels that can open patient's periodontal pocket and wash out and suck out plaque therein; when the cap 321 is screwed midway onto the pipe 310, the water ejects out from the pinhole 322 and forms a twisted water stream that can cleanse a tooth extraction site or irrigate an exposed jawbone.

Thus, specific embodiments and applications of 7-way dental syringe have been disclosed. It should be apparent, however, to those skilled in the art that many more modifications beside those already described are possible without departing from the inventive concepts herein. The inventive subject matter, therefore, is not to be restricted except in the spirit of the appended claims. Moreover, in interpreting both the specification and the claims, all terms should be interpreted in the broadest manner possible consistent with the context, In particular, the terms "comprises" and "comprising" should be interpreted as referring to elements, components, or steps in a non-exclusive manner, indicating that the referenced elements, components, or steps may be present or utilized, or combined with other elements, components or steps that are not expressly referenced.

What is claim is:

1. A seven-way dental syringe for attachment to a dental delivery system in a dental office, said dental syringe comprising double lumen tubing, a handle, and an exchangeable tip;

said double lumen tubing having a first conduit for air and a second conduit for water, said first and second conduits are adapted to deliver air and water from said dental delivery system under pressure;

said handle comprising an elongated body having first and second opposite ends, a fluid passageway and a tip connector; wherein the fluid passageway extends through said elongated body from said first end to said second end, said fluid passageway is comprised of an air passageway for conveying air from said first conduit, a water passageway for conveying water from said second conduit and a merged passageway where the water passageway and air passage are combined to provide a merged flow from said body second end: wherein the air passageway includes an on/off air valve; wherein the water passageway includes a flow volume controllable water valve which can adjust water pressure from said body from zero to a maximum; and wherein the tip connector is at the second end of said body for connecting said tip to the merged passageway;

said the tip having a bent pipe, an adapter and a twist generator; said pipe is a conduit to transfer air and/or water from said handle to said twist generator; said adapter for securing connection of said tip to said tip connector of said handle; wherein the twist generator comprises a closed-off distal end of the pipe having a male external thread, a cap having internal thread and a pinhole centrally located at the top end of said cap, and an opening arrangement in the pipe distal end that divides the fluid flow from the pipe distal end into two separate flows and twists them;

wherein for advanced oral hygiene an operator turns said water valve to the maximum position when said cap is screwed tightly against said pipe, twisted water ejects out from said pinhole shaped as a fast rotating water hollow cone for accessing a user's periodontal pocket to wash out any plaque therein and sucking out any plaque therein; when said cap is screwed loose against said pipe, water ejects out from said pinhole in the form of a twisted beam for cleansing a user's teeth and interdental regions; and when said cap is screwed semi-tight against said pipe, water ejects out from the said pinhole in the form of a twisted stream for cleansing a tooth extraction site or irrigating exposed jawbone;

wherein said tip can also eject out an air stream, an air spray, a water stream and a water spray having various pressure for effectively cleaning away debris from the area that a dentist is working on.

* * * * *